US011357889B2

United States Patent
Awad et al.

(10) Patent No.: US 11,357,889 B2
(45) Date of Patent: Jun. 14, 2022

(54) NATIVE SOFT TISSUE MATRIX FOR THERAPEUTIC APPLICATIONS

(71) Applicants: Hani Awad, Rochester, NY (US); Bradley T. Estes, Durham, NC (US); Farshid Guilak, Clayton, MO (US)

(72) Inventors: Hani Awad, Rochester, NY (US); Bradley T. Estes, Durham, NC (US); Farshid Guilak, Clayton, MO (US)

(73) Assignee: Cytex Therapeutics, Inc., Durham, NC (US)

( * ) Notice: Subject to any disclaimer, the term of this patent is extended or adjusted under 35 U.S.C. 154(b) by 782 days.

(21) Appl. No.: 15/444,445

(22) Filed: Feb. 28, 2017

(65) Prior Publication Data

US 2017/0165400 A1     Jun. 15, 2017

Related U.S. Application Data

(63) Continuation of application No. 10/874,402, filed on Jun. 23, 2004, now abandoned.

(51) Int. Cl.
| | |
|---|---|
| A61L 27/36 | (2006.01) |
| A61F 2/00 | (2006.01) |
| A61F 2/02 | (2006.01) |
| A61L 2/08 | (2006.01) |
| A61L 27/38 | (2006.01) |
| A61L 27/54 | (2006.01) |
| A61L 27/56 | (2006.01) |

(52) U.S. Cl.
CPC ........ *A61L 27/3612* (2013.01); *A61F 2/0022* (2013.01); *A61F 2/0036* (2013.01); *A61F 2/02* (2013.01); *A61L 2/081* (2013.01); *A61L 27/3804* (2013.01); *A61L 27/3817* (2013.01); *A61L 27/3834* (2013.01); *A61L 27/54* (2013.01); *A61L 27/56* (2013.01); *A61F 2210/0004* (2013.01); *A61F 2210/009* (2013.01); *A61F 2240/001* (2013.01); *A61F 2250/0004* (2013.01); *A61F 2250/0068* (2013.01); *A61L 2202/21* (2013.01); *A61L 2400/06* (2013.01); *A61L 2430/06* (2013.01); *A61L 2430/34* (2013.01)

(58) Field of Classification Search
CPC ............. A61L 27/3608; A61L 27/2612; A61L 27/3629
See application file for complete search history.

(56) References Cited

U.S. PATENT DOCUMENTS

| | | | | |
|---|---|---|---|---|
| 2002/0099448 | A1* | 7/2002 | Hiles ..................... | A61F 2/0095 623/23.61 |
| 2003/0206937 | A1* | 11/2003 | Gertzman .............. | A61K 35/32 424/426 |
| 2004/0091462 | A1* | 5/2004 | Lin ..................... | A61L 27/3608 424/93.7 |

OTHER PUBLICATIONS

Jackson "Bone Banking: an overview" Laboratory Medicine, 1987, vol. 18, No. 12, pp. 830 (Year: 1987).*
"Pulverize." Merriam-Webster.com. Merriam-Webster, n.d. Web. Jul. 25, 2018. (Year: 2018).*
Matrix, (n.d.) Farlex Partner Medical Dictionary. (2012). Retrieved Jul. 26, 2018 from https://medical-dictionary.thefreedictionary.com/matrix (Year: 2012).*
"Homogenize." Merriam-Webster.com. Merriam-Webster, n.d. Web Jul. 25, 2018. (Year: 2018).*
"Precipitate." Merriam-Webster.com. Merriam-Webster, n.d. Web. Apr. 3, 2019 (Year: 2019).*
Sigma-Aldrich "Tissue Homogenizers" Labware Product Directory. Retrieved on Dec. 20, 2019 from https://www.sigmaaldrich.com/labware/labware-products.printerview.html?TablePage=9577097 (3 pages) (Year: 2019).*

* cited by examiner

*Primary Examiner* — Allison M Fox
(74) *Attorney, Agent, or Firm* — Maginot Moore Beck LLP

(57) ABSTRACT

A method is used for preparing a product for use in repairing a lesion or defect at a tissue site in a human or animal patient body. The method includes obtaining tissue from a donor human or animal body and freezing the obtained tissue. The method further includes pulverizing the frozen tissue and suspending the pulverized tissue in a fluid. The method further includes homogenizing the tissue suspension and precipitating tissue particles from the homogenized tissue suspension. The method further includes re-suspending the precipitated tissue particles and lyophilizing the tissue re-suspension to provide the product to be used in repairing the lesion or defect.

18 Claims, No Drawings

NATIVE SOFT TISSUE MATRIX FOR THERAPEUTIC APPLICATIONS

CLAIM OF PRIORITY

This application is a continuation application of U.S. patent application Ser. No. 10/874,402, filed on 23 Jun. 2004, having the name Native Soft Tissue Matrix for Therapeutic Applications.

BACKGROUND OF THE INVENTION

The present invention relates to the repair, replacement and/or regeneration of diseased or traumatized soft tissue.

Tissue and organ failure represents a major socioeconomic burden and has been estimated to cost the economy over $400 billion per year. Numerous approaches are being developed in an effort to promote the repair or regeneration of tissues or organs. Recent studies suggest that the introduction of autologous or allogeneic tissues, with or without the addition of biologically active molecules such as growth factors, may have the ability to promote new tissue formation and serve as a material for cellular infiltration and tissue repair in the body. For example, Urist and co-workers have shown the potential for the induction of bone in ectopic sites such as muscle by the implantation of demineralized bone powder. See, Urist et al., *Bone formation in implants of partially and wholly demineralized bone matrix*, Clin. Orthop.71:271-8 (1970) (including observations on acetone-fixed intra and extracellular proteins). This approach served as the basis of the discovery of specific molecules present in the non-mineral portion of bone, termed "bone morphogenetic proteins", which have since been shown to be potent promoters of bone regeneration.

While this approach suggested by Urist et al. has proven valuable for applications involving bone regeneration and repair, a similar approach is not available for the repair of soft tissues such as cartilage, meniscus, intervertebral disc, muscle, tendon/ligament, blood vessels, nerve, or other tissues. The repair of these soft tissues following degeneration, disease, or injury remains a major challenge to the medical field. In particular, avascular tissues such as the cartilaginous tissues show little or no intrinsic repair capacity. It is believed that the directed repair of these tissues will require an approach that is enhanced by biomaterials and biologically active molecules.

In such cases, there is often a need to replace missing or damaged tissues with functional tissue replacements. The current state of the art typically involves the use of autologous tissue grafts, cryo-preserved or fresh allograft tissues, or the use of synthetic (metal, polymer) replacement materials. Autogenous tissue is often limited in availability and is generally associated with significant donor site morbidity. Fresh allograft tissues are associated with significant risks of disease transmission, while intact but radiation sterilized allografts suffer a loss of biomechanical function and generally do not support repopulation by the host's cells, and therefore show limited long-term success. See, e.g., Rasmussen et al., *The effects of 4 Mrad of gamma irradiation on the initial mechanical properties of bone-patellar tendon-bone grafts*, Arthroscopy, Apr.10(2):188-97 (1994).

Synthetic implants, on the other hand, have a limited fatigue life and often introduce problems of wear or integration in the body. Previous approaches have also implanted intact allograft tissues, but have shown minimal host cell infiltration, and thus significant tissue necrosis and degradation occurs over time. Thus, there are no satisfactory approaches currently available for the long-term repair of soft tissue injury or disease.

SUMMARY OF THE INVENTION

One important aspect of the present invention is to process soft tissue from specific sites in the body in a manner that produces pulverized morsels of the soft tissue devoid of immunogenic material and pathogens but with intact aspects of the composition of the extracellular matrix proteins including the growth factors and cytokines that are responsible for tissue growth and cellular infiltration and differentiation. This pulverized soft tissue in the form of morsels, hereafter Native Soft Tissue Matrix or NSTM, may be implanted or injected at the needed site(s) in the body. Alternatively, the NSTM may be combined with other known biomaterials, which are biologic, synthetic or a combination of the two prior to therapeutic use. The resulting composite, taking the form of a slurry or paste, may then be implanted or injected at the needed site(s) in the body. Alternatively, the NSTM composite can be reconstituted as a tissue scaffold to promote the ex vivo regeneration of various tissues which can then be implanted in the body. The development of a variety of biomaterial matrices that are biologic, synthetic or a combination of the two based on specific tissues of the body will provide an efficient and effective approach for promoting tissue repair using either cellular or acellular approaches.

In a further aspect of the invention, the NSTM may also be used to deliver cells and/or additional, exogenously introduced biologically active molecules, such as growth factors, cytokines, chemokines, antibiotics, DNA, other molecules that may induce directed growth and/or differentiation of cells, or vectors capable of delivering bioactive therapeutic genes to the product.

The present invention introduces the use of a native soft tissue matrix in the form of morsels that can be used either as an acellular (non-viable) filler material or combined with viable elements (cells) and/or bioactive molecules to promote the repair or regeneration of diseased or traumatized soft tissues. In an important aspect of the invention, the soft tissue product is non-mineralized, meaning that it is derived from body tissues that are essentially non-mineral in nature. Thus, the soft tissue product of this invention excludes tissues such as bone and teeth as sources of the NSTM.

DESCRIPTION OF THE PREFERRED EMBODIMENTS

For the purposes of promoting an understanding of the principles of the invention, reference will now be made to the embodiments described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

This invention disclosure describes a native soft tissue matrix (NSTM) that can be used either as an acellular (non-viable) matrix or combined with viable elements (cells) and/or bioactive molecules (growth factors (GF)) for use as an implantable product in repair/replacement/regeneration of diseased or traumatized soft tissue and/or tissue engineering applications.

The NSTM according to this invention is derived from the soft tissues of the body, potentially to repair/replace/regenerate the same tissues. The NSTM is substantially non-mineralized meaning that it consists essentially of tissues or organs other than bone, teeth or other mineralized biologic materials. Suitable soft tissues include, but not limited to, any of the following:

a) Cartilage
b) Meniscus
c) Intervertebral Disc (IVD)
d) Ligament
e) Tendon
f) Muscle
g) Fascia
h) Periosteum
i) Perichondrium
j) Pericardium
k) Skin
l) Nerve
m) Blood vessels
n) Heart valves
o) Bladder
p) Lung Additional possibilities for sources of tissue may include organs such as the kidney, liver, pancreas, thyroid, or thymus.

The NSTM can be derived from autologous, allogeneic, or xenogeneic tissues or organs. Preferably, the NSTM is devitalized using a sequence of steps aimed at producing a pathogen-free, immunologically-tolerable matrix. These steps can include treatments commonly used by tissue banks, such as treatment with DNAase and RNAase solutions, sequential washing in PBS, freeze-drying (lyophilizing), and sterilization using gamma-rays.

The NSTM is provided in a form that allows its introduction or implantation within a soft tissue site requiring repair and/or augmentation. The NSTM can be prepared in the form of a dry powder, dry morsels, frozen paste, or frozen slurry for reconstitution at the point-of-care or at processing/manufacturing facilities. In a preferred embodiment, the NSTM is reconstituted at the point-of-care in solution as a viscous gel in various concentrations (0.1%-99% w/v) to mimic the native tissue composition. The viscous gel can then be used as an injectable therapeutic product. Alternatively, the NSTM can be provided in a moldable carrier. For example, in one embodiment, the NSTM is mixed with a biologic human or animal-derived flowable material, such as a viscous gel carrier, which can be easily injected into a pathological site (for instance a debrided lesion). In a preferred embodiment, the flowable carrier is a collagen or a gelatin. Preferably, the flowable material is selected from the group consisting of collagen, gelatin, blood derivatives, plasma, synovial fluid, serum, hyaluronic acid, proteoglycans and elastin.

In alternative embodiments, the biomaterial carrier can be composed of any of the following materials:

a) Biological non-human in situ cross-linkable gels such as alginate or agarose, or xenograft derived gels.
b) Synthetic cross-linkable polymers such as PEO/PEG polymers.
c) Synthetic resorbable polymers such as PLA, PGA, PLDLA, and PCL. With this embodiment, as the polymer resorbs over time, an increasing amount of NSTM will become active (via exposure) and aid in the healing process.
d) A synthetic and biologic (human or animal) mixture (or composite) of any of the aforementioned types of materials.

In certain embodiments, the NSTM may be bound to a porous, woven or non-woven, biodegradable or biocompatible (non-degradable) scaffold of predetermined geometry and dimensions using any combination of materials listed. The size and geometry of the scaffold is determined by the soft tissue site into which the product is introduced.

In still other embodiments, the NSTM can be reconstituted as a porous solid scaffold of predetermined geometry and dimensions which can be used as a transplantable therapeutic product. The scaffold can be fabricated by casting a viscous gel (of the type described above) into molds, cross-linking the cast gel using known techniques, such as UV light, non-enzymatic glycation, tissue transglutaminase, or other crosslinking methods, and then freeze-drying the cast gel under vacuum to create a porous scaffold. The pore size can be controlled by manipulating the solid fraction, rate of freezing, and vacuum applied. The pore orientation (degree of anisotropy) can be controlled by manipulating the direction of the applied vacuum.

The reconstituted NSTM in any of the configurations above can be combined with the patient's own cells (autologous), cells from another individual (allogeneic), or cells from other species (xenogeneic), all of which may be genetically modified. The cells can be differentiated, phenotype-specific cells, committed progenitor cells, or toti-, pluri- or multi-potential stem cells. When used in combination with cells, marrow, and/or blood derivatives, the NSTM preferably provides a phenotypic substrate and intact aspects of the composition of the extracellular matrix proteins including the growth factors and cytokines to guide cell and tissue differentiation, growth, and remodeling. This reconstituted NSTM can further be combined with the patient's own bone marrow, blood, serum, or a concentrate of blood-derived growth factors at the point-of-care or in a manufacturing facility. Similarly, the reconstituted NSTM may be combined with bioactive molecules including various growth factors such as TGF-β, IGF, bFGF, PDGF, VEGF, and/or BMP.

DESCRIPTION OF SPECIFIC EMBODIMENTS

As examples, the following section describes methods of the present invention that can be used to create a devitalized native soft tissue matrix derived from cartilage (NSTM-CH) that can be provided to a point-of-care facility, or to processing or manufacturing facilities in various formulations. These formulations, including dry powder, dry morsels, frozen paste, or frozen slurry, can be reconstituted alone or in combination with cells, a carrier material, or bioactive molecules. The reconstituted NSTM-CH is used to repair cartilage focal defects or damage, or osteoarthritis-related lesions. It is understood that no limitation to the scope or the application of the methods of the current invention to cartilage repair is thereby intended. Rather, the methods of the current invention can be extended to include applications for repair of all soft tissues from which the NSTM can be derived including meniscus, intervertebral disc, ligament, tendon, muscle, fascia, periosteum, perichondrium, skin, nerve, blood vessels, bladder, lung, and heart valves. It is also understood that the NSTM derived from any of the above soft tissue and organs can be used to repair any of the above listed soft tissues and organs, as well as mineralized tissues such as bone.

In one embodiment, a specific formulation of an allogeneic NSTM-CH is combined with cells, chondro-inductive growth factors, and a carrier material that can have the form of a hydrogel or a porous scaffold. In this embodiment, the NSTM-CH serves as the biological substrate onto which the cells can proliferate, differentiate, and synthesize competent cartilage matrix.

The cells used in this application are: 1) chondrocytes, which can be isolated from different autologous sources (such as articular cartilage, elastic cartilage, or epiphysial growth-plate) by enzymatic digestion (e.g. collagenase and pronase); 2) mesenchymal stem cells isolated and propagated from the patients bone marrow; 3) adipose-derived adults stem cells isolated from fat tissue biopsies from the same patient; or 4) other sources of toti-, multi- or pluri-potential stem cells. The isolation and propagation of these cells might require the use of cell culture facilities remote from the point-of-care facility and in some cases extended processing time. In an alternate embodiment, bone marrow is directly used as a heterogeneous suspension of cells containing stem cells. A further alternative is to concentrate a specific population of cells in a density gradient in bone marrow and re-suspend them in a nutrient-rich medium at the point-of-care.

The carrier material can be a moldable biologic material or a porous scaffold. The carrier material provides a means for effective delivery, structural enforcement, and/or predetermined geometry guidance. In the preferred embodiment, the moldable biologic material is a hydrogel carrier material. Suitable hydrogel materials may include: 1) biological gels such as collagen, hyaluronic acid, fibrin, gelatin, elastin or other biological materials; 2) marine organism-derivatives such as, alginate, agarose, or chitosan gels; or 3) synthetic hydrogels such as Pluronic/F-12 and PEO/PEG gels. This carrier material is moldable so that the product can be configured to match the contours of the soft tissue site in which the product is to be implanted.

Alternately, the carrier material may be a porous, woven or non-woven, biodegradable or biocompatible (non-degradable) scaffold of predetermined geometry and dimensions made from biological or man-made polymers including but not limited to gelatin mesh, collagen mesh, polyglycolic acid, polylactic acid, polyorthoesters, polyglycolide-co-lactides, polyanhydrides, poly(amino acids), pluronic/F-12, PEO/PEG, polycaprolactones or other suitable synthetic hydrogels or mixtures thereof. In certain applications, a composite matrix made from a hydrogel and a porous scaffold may be appropriate.

In certain embodiments, the carrier material includes a non-resorbable and non-biodegradable constituent. The constituents are selected from the group consisting of acrylics, polycarbonates, polyesters, polyethers, poly(ether ketone), poly(ether, ether ketone), poly(aryl ether ketones), poly(ether ether ketone ether ketone), poly(ethylene terephthalate), poly(methyl (meth)acrylate), polyolefins, polysulfones, polyurethane, polyethylene, polypropylene, poly(vinyl chloride), fiber reinforced composites, or mixtures thereof.

The chondro-inductive factors may include growth factors with demonstrated chondro-inductive effects including but not limited to TGF-$\beta$, IGF, bFGF, and/or BMPs and combinations thereof. These growth factors can be obtained using recombinant technology from pharmaceutical suppliers or can be isolated and concentrated from the patient's own blood, serum, or bone marrow at the point-of-care.

The following specific examples are provided to illustrate the methods and materials of the present invention as they apply to cartilage. Other applications can be easily extrapolated using either identical or similar techniques to repair intervertebral disc, ligament, tendon, muscle, or any of the other tissues listed in this disclosure. Although derived from non-mineralized tissues, the NSTM may also be used to promote the repair of any mineralized tissues such as bone. Suitable modifications and adaptations of the variety of conditions and parameters normally encountered in surgical situations which are obvious to those skilled in the art are within the spirit and scope of the present invention. It is understood that all methods described within are to be performed in strict adherence to sterile cell culture techniques and good laboratory/manufacturing practices. All reagents and solutions used shall be sterile.

EXAMPLE 1

Acellular NSTM-CH Slurry for Injection into Cartilage or other Soft Tissue Lesions Preparation of the NSTM-CH Dry Formulation:

Human cartilage from tissue banks or from trauma patients, obtained in accordance with standards and ethics appropriate for the handling of human tissue, is minced into small pieces (1-5 mm2) and then incubated at 37° C. in 50 ml test tubes containing phosphate buffered saline ("PBS") and 10% of Penicillin/Streptomycin/Fungizone or similar antibiotic/antimycotic solutions for 1-2 hours. The cartilage pieces are then washed thoroughly in PBS, after which the PBS is removed and discarded, and the cartilage pieces are snap frozen in $LN_2$. The frozen cartilage specimens are then crushed using a cryogenic tissue pulverizer, such as the Bio-Pulverizer™ of BioSpec Products, Inc., or similar tissue grinders/mills.

In a preferred embodiment of the invention, the tissue is pulverized to a particle size that is insufficient as a scaffold to be populated by native cells. Instead, the particle size is limited to a size effective to provide differentiation cues for the native cells of the soft tissue site in which the product of the present invention is implanted. In the preferred embodiment, the particle size is less than about 800 µm. In a more specific embodiment, the particle size is limited to a range of 1-100 µm.

The pulverized tissue is then placed in polypropylene tubes and suspended in an appropriate volume of distilled water ($dH_2O$). The pulverized tissue suspension is then further homogenized using a tissue homogenizer. The homogenized tissue suspension is centrifuged, the supernatant removed, and the precipitate tissue particles are re-suspended and incubated at 37° C. in an enzymatic solution containing DNAase and RNAase to remove DNA and RNA proteins which can potentially induce an immunogenic response in the host joint. After treatment with DNAase and RNAase, the tissue suspension is centrifuged and washed several times in $dH_2O$ to remove traces of the enzymes. The tissue is then re-suspended in $dH_2O$, mixed well, and then snap frozen in $LN_2$. The frozen homogenized tissue tubes are then freeze dried or lyophilized to produce a dry form of the devitalized native cartilage matrix. The aseptically derived dried formulation may then be additionally sterilized by gamma irradiation or similar sterilization techniques. The dried formulation is provided to the surgeon at the point-of-care in a sterile vial as an off-the-shelf allogeneic devitalized biomatrix to be used in indications such as trauma-induced focal cartilage lesions, osteoarthritic lesions, and other cartilage pathologies.

Reconstitution and Surgical Injection of the NSTM-CH as Hydrated Slurry:

At the point-of-care, the surgeon reconstitutes the dry formulation of NSTM-CH in an appropriate volume of saline or a pharmaceutical solution of chondro-inductive growth factors such that the concentration of the reconstituted slurry is, for example, ~20% (w/v). The surgeon then implants the hydrated slurry into the defect in a surgical repair procedure (See e.g., Brittberg et al., Treatment of deep cartilage defects in the knee with autologous chondrocyte transplantation. N Engl J Med 1994;331:889-95.). During surgery, the surgeon may carefully remove the damaged tissue and prepare the lesion for the injection of the reconstituted NSTM-CH. A small patch of fascia obtained from the patient's joint capsule is sutured over the lesion and its edges sealed with biological glue (e.g., fibrin) to hold the viscous slurry in place. Alternately, a piece of periosteum obtained from the patient's bone can be used as a patch cover for the lesion. The hydrated slurry is then injected under the fascia patch into the lesion where the devitalized NSTM-CH can provide biological cues to attract and guide the differentiation of migrating cells from the host cartilage, subchondral bone, and/or bone marrow.

EXAMPLE 2

Synovial/NSTM-CH Slurry for Injection into Cartilage or other Soft Tissue Lesions At the point-of-care, the surgeon reconstitutes the dry formulation of NSTM-CH in an appropriate volume of synovial fluid drawn from the patient's healthy joint, such that the concentration of the reconstituted slurry is, for example, ~10-20% (w/v). Alternately, the NSTM-CH can be reconstituted in a pharmaceutical viscous synovial supplement (e.g., Synvisc® Hylan G-F 20 produced by Genzyme Corporation). The surgeon then implants the viscous slurry into the defect in a surgical repair procedure as described in example 1.

EXAMPLE 3

Serum/NSTM-CH Slurry for Injection into Cartilage or other Soft Tissue Lesions

At the point-of-care, the surgeon draws an appropriate volume of the patient's blood and collects the blood serum or blood plasma using established protocols. The surgeon then reconstitutes the dry formulation of NSTM-CH in an appropriate volume of serum or plasma, such that the concentration of the reconstituted slurry is, for example, ~10-20% (w/v). The surgeon then implants the reconstituted slurry into the defect in a surgical repair procedure as described in example 1.

EXAMPLE 4

Chondrocyte/NSTM-CH Suspension for Injection into Cartilage or other Soft Tissue Lesions A biopsy of hyaline, elastic, or fibro-cartilage is obtained from the patient from a variety of cartilage sources in the body including, but not limited, to non-load bearing articular cartilage, nasal cartilage, costal cartilage, auricular cartilage, physea (growth plate) cartilage, and tracheal cartilage. The cartilage biopsy is placed inside tubes containing culture media. The tubes are sealed sterile and sent on ice (~4° C.) to the processing facility where cartilage is then sliced into small bits measuring approximately 2 mm in length and width. The cartilage is incubated at 37° C. in 50 ml test tubes containing Dulbecco's modified medium ("DMEM") or other appropriate media and 10% of Penicillin/Streptomycin/Fungizone or similar antibiotic/antimycotic solutions for 30 minutes. The wash media is aspirated, and the minced tissue is incubated for an hour at 37° C. in a DMEM solution containing the nonspecific enzyme pronase (~10,000 PUK/gram of tissue) with intermittent mixing. The pronase solution is then removed and the tissue is further incubated at 37° C. for 2-3 hours with a collagenase type-2 solution (~0.4% (w/v)) in DMEM with intermittent mixing, until the cartilage bits have completely been digested. The isolated chondrocyte suspension is then passed through a 70 micron nylon mesh cell strainer to remove undigested bits of cartilage. The strained cell suspension is centrifuged, washed in PBS to remove traces of the enzyme, and prepared for use immediately or plated in appropriate culture conditions to increase cell yield. The viable cells are then shipped back to the point-of-care.

At the point-of-care, the chondrocytes are brought into suspension in a chondrogenic formulation of media, saline, a pharmaceutical solution of growth factors, serum, plasma, or synovial fluid or supplement. The cell suspension is them mixed with the dry formulation of NSTM-CH such that the concentration of the NSTM-CH component in the reconstituted suspension is, for example, ~10-20% (w/v). The surgeon then implants the reconstituted cell suspension into the defect in a surgical repair procedure as described in example 1.

As an alternative, fully differentiated phenotype specific cells for the specific tissue that is being replaced could be substituted in this example for the repair of other soft tissues. For instance, annular fibrosus cells or nucleus pulposus cells would be used if the targeted repair is located in the intervertebral disc. However, it should be noted that chondrocytes, or non-phenotypic cells may also be used to treat pathology in different soft tissues from which they are derived.

EXAMPLE 5

MSC/NSTM-CH Suspension for Injection into Cartilage or other Soft Tissue Lesions At the point-of-care, the surgeon obtains a bone marrow biopsy from the patient. A density gradient is used to eliminate unwanted cell types present in the marrow aspirate. The small percentage of mesenchymal cells (MSC) isolated using the density gradient are brought into suspension in a chondrogenic formulation of media, saline, a pharmaceutical solution of growth factors, serum, plasma, or synovial fluid or supplement. The cell suspension is them mixed with the dry formulation of NSTM-CH such that the concentration of the NSTM-CH component in the reconstituted suspension is ~10-20% (w/v). The surgeon then implants the reconstituted cell suspension into the defect in a surgical repair procedure as described in example 1.

EXAMPLE 6

ADAS/NSTM-CH Suspension for Injection into Cartilage or other Soft Tissue Lesions An aspirate of adipose tissue obtained from the patient using a liposuction procedure is sent to the processing/manufacturing facility. Adipose-derived adult stem (ADAS) cells are isolated from the stromal vascular fraction of the lipoaspirates using a collagenase digestion protocol. The cells are propagated in culture and then retrieved and shipped back to the point-of-care. The isolated cells are then shipped back to the point-of-care.

The ADAS cells are brought into suspension in a chondrogenic formulation of media, saline, a pharmaceutical solution of growth factors, serum, plasma, or synovial fluid or supplement. The cell suspension is them mixed with the dry formulation of NSTM-CH such that the concentration the NSTM-CH component in the reconstituted suspension is, for example, ~10-20% (w/v). The surgeon then implants the reconstituted cell suspension into the defect in a surgical repair procedure as described in example 1.

EXAMPLE 7

Cell/Hydrogel/NSTM-CH Suspension for Injection into Cartilage or other Soft Tissue Lesions At the point-of-care, cells (which could be chondrocytes, MSCs, ADAS cells, or other chondroprogenitor cells) are brought into suspension in a chondrogenic formulation of media, saline, a pharmaceutical solution of growth factors, serum, plasma, or synovial fluid or supplement. The cell suspension is them mixed with the dry formulation of NSTM-CH such that the concentration of the NSTM-CH component in the reconstituted suspension is, for example, ~10-20% (w/v). The cell/NSTM-CH suspension is mixed with a pharmaceutical grade hydrogel at an appropriate concentration. The preferred form of the hydrogel is an in situ cross-linkable material which can be mixed with the cell/NSTM-CH suspension, injected into the lesion as described in example 1, and cross-linked by means of a change in temperature (e.g., agarose, pluronic F-127), pH (e.g., collagen), ionic bond formation (e.g., alginate) or enzymatic cross-linking pathway (e.g., fibrin).

EXAMPLE 8

Porous Scaffold/NSTM-CH for Implantation into Cartilage or other Soft Tissue Lesions Porous, woven or non-woven, synthetic or biological polymer scaffolds are used in this example to provide structural support and geometrical control and guidance. The scaffold is preferably degradable and could be made from gelatin mesh, collagen mesh, polyglycolic acid, polylactic acid, glycolide-co-lactide, polyanhydride, polycaprolactone scaffolds, or other biological or synthetic polymers. At the point-of-care, cells (which could be chondrocytes, MSCs, ADAS cells, or other chondroprogenitor cells) are brought into suspension in a chondrogenic formulation of media, saline, a pharmaceutical solution of growth factors, serum, plasma, or synovial fluid or supplement. The cell suspension is them mixed with the dry formulation of NSTM-CH such that the concentration the NSTM-CH component in the reconstituted suspension is, for example, ~10-20% (w/v). The cell/NSTM-CH suspension is seeded onto the porous scaffold.

The surgeon then prepares the defect bed to match the geometry and dimensions of the scaffold and the cell/NSTM-CH-laden scaffold is implanted into the bed. A small patch of fascia obtained from the patient's joint capsule is sutured over the implant and its edges sealed with biological glue (e.g., fibrin) to prevent leakage of the cell/NSTM-CH suspension. In this embodiment, the NSTM-CH serves to provide biological cues to guide cell differentiation and neomatrix formation whereas the porous scaffold provides structural support, geometrical control and growth guidance.

Alternately, the cells, NSTM-CH, and scaffold can be coaxed into a tissue-engineered (TE) cartilage implant at a remote processing/manufacturing facility. The TE cartilage implant is cultured in a closed-system bioreactor by which physical and chemical chondrogenic factors are controlled to produce a consolidated TE cartilage implant, which can then be shipped to the point-of-care for implantation.

While the invention has been illustrated and described in detail in the foregoing description, the same should be considered as illustrative and not restrictive in character. It is understood that only the preferred embodiments have been presented and that all changes, modifications and further applications that come within the spirit of the invention are desired to be protected.

For example, other applications can be extrapolated using either identical or similar techniques to repair intervertebral disc, ligament, tendon, muscle are any of the other soft, non-mineralized tissues listed in this disclosure. Suitable modifications and adaptations of the variety of conditions and parameters normally encountered in surgical situations which are obvious to those skilled in the art are within the spirit and scope of the present invention.

What is claimed is:

1. A method for preparing a product for use in repairing a lesion or defect at a tissue site in a human or animal patient body, the method comprising:
   obtaining tissue from a donor human or animal body;
   freezing the obtained tissue;
   pulverizing the frozen tissue;
   suspending the pulverized tissue in a fluid;
   homogenizing the tissue suspension using a tissue homogenizer;
   precipitating tissue particles from the homogenized tissue suspension;
   re-suspending the precipitated tissue particles; and
   lyophilizing the tissue re-suspension to provide the product to be used in repairing the lesion or defect.

2. The method of claim 1, further comprising:
   rehydrating the lyophilized tissue to form a slurry.

3. The method of claim 2, further comprising:
   forming a porous solid scaffold consisting of the slurry.

4. The method of claim 3, wherein:
   forming the porous solid scaffold includes molding the slurry to have a size and geometry determined by the tissue site.

5. The method of claim 4, wherein:
   molding the slurry includes:
      casting the slurry into a mold,
      cross-linking the cast slurry, and
      freeze-drying the cross-linked slurry.

6. The method of claim 1, wherein:
   the obtained tissue is a substantially non-mineralized soft tissue.

7. The method of claim 6, wherein:
   the substantially non-mineralized soft tissue is a same type of tissue as a tissue at the tissue site in the human or animal patient body.

8. The method of claim 1, wherein:
   pulverizing the frozen tissue includes pulverizing the frozen tissue to form particles having a particle size of less than about 800 μm.

9. The method of claim 8, wherein the particle size is in a range of 1 μm to 100 μm.

10. The method of claim 1, further comprising:
   freezing the tissue re-suspension prior to lyophilizing the tissue re-suspension.

11. The method of claim 1, further comprising:
mincing the obtained tissue into pieces prior to freezing the obtained tissue.

12. The method of claim 11, wherein:
the pieces have a piece size in a range of 1 mm$^2$ to 5 mm$^2$.

13. A method for repairing a lesion or defect at a tissue site in a human or animal patient body, the method comprising:
obtaining tissue from a donor human or animal body;
freezing the obtained tissue;
pulverizing the frozen tissue;
suspending the pulverized tissue in a fluid;
homogenizing the tissue suspension using a tissue homogenizer;
precipitating tissue particles from the homogenized tissue suspension;
re-suspending the precipitated tissue particles;
lyophilizing the tissue re-suspension to form a dry formulation;
reconstituting the dry formulation to form a slurry; and
implanting the slurry into the lesion or defect at the tissue site in the human or animal patient body.

14. The method of claim 13, further comprising:
forming a porous solid scaffold of the slurry,
wherein implanting the slurry into the lesion or defect includes implanting the porous solid scaffold into the lesion or defect.

15. The method of claim 13, further comprising:
binding the slurry to a scaffold,
wherein implanting the slurry into the lesion or defect includes implanting the scaffold into the lesion or defect.

16. The method of claim 13, further comprising:
combining the slurry with cells,
wherein implanting the slurry into the lesion or defect includes implanting the slurry-cell combination into the lesion or defect.

17. The method of claim 13, further comprising:
combining the slurry with exogenously introduced biologically active molecules,
wherein implanting the slurry into the lesion or defect includes implanting the slurry-molecule combination into the lesion or defect.

18. The method of claim 13, further comprising:
obtaining a fluid from the human or animal patient body,
wherein reconstituting the dry formulation includes reconstituting the dry formulation with the fluid from the human or animal patient body to form the slurry.

* * * * *